United States Patent [19]

Olivier et al.

[11] Patent Number: 4,777,034

[45] Date of Patent: Oct. 11, 1988

[54] COMPOSITIONS FOR COUNTERACTING THE DEGRADATIONS AND INCONVENIENCE OF PERSPIRATION

[76] Inventors: Georges R. G. Olivier; Simone A. M. H. Olivier, both of 12 Bis Route de Nantes, 85340 Olonne S/Mer, France

[21] Appl. No.: 113,377

[22] Filed: Oct. 29, 1987

Related U.S. Application Data

[63] Continuation of Ser. No. 821,879, Jan. 27, 1986, abandoned, and a continuation of Ser. No. 481,241, Apr. 1, 1983, abandoned.

[30] Foreign Application Priority Data

Apr. 1, 1982 [FR] France ............................ 82 05898

[51] Int. Cl.$^4$ .................. A61K 7/32; A61K 7/34; A61K 7/36; A61K 7/38
[52] U.S. Cl. ......................................... 424/65; 424/66; 424/67; 424/68; 424/69; 514/947; 514/949
[58] Field of Search .................. 424/66, 67, 68, 65

[56] References Cited

U.S. PATENT DOCUMENTS

| | | | |
|---|---|---|---|
| 3,275,643 | 9/1966 | Lubowe | 424/65 X |
| 4,172,123 | 10/1979 | Lourcki | 424/68 |
| 4,302,443 | 11/1981 | de Navarre | 424/68 |

FOREIGN PATENT DOCUMENTS

| | | | |
|---|---|---|---|
| 1068215 | 12/1979 | Canada | 424/68 |
| 2224127 | 10/1974 | France | 424/65 |
| 2394290 | 2/1979 | France | 424/68 |
| 2498451 | 7/1982 | France | 424/59 |
| 1492036 | 2/1969 | Fed. Rep. of Germany | 424/59 |
| 1492023 | 12/1973 | Fed. Rep. of Germany | 424/59 |
| 2901069 | 7/1979 | Fed. Rep. of Germany | 424/65 |
| 2826759 | 12/1979 | Fed. Rep. of Germany | 424/65 |
| 0083612 | 5/1983 | Japan | 424/65 |
| 514979 | 11/1939 | United Kingdom | 424/65 |
| 880276 | 10/1961 | United Kingdom | 424/59 |

*Primary Examiner*—Dale R. Ore
*Attorney, Agent, or Firm*—Oblon, Fisher, Spivak, McClelland & Maier

[57] ABSTRACT

Composition enabling the degradations and inconveniences of perspiration to be counteracted, said composition comprising at least one anti-absorbant agent and/or an antiseptic agent and/or an anti-sweating agent and/or an antiseptic agent and/or an antimycotic agent and/or an anti-irritant agent and/or an antifungal agent and/or an anti-putrid agent and/or a deodorant and/or a nutrient agent and/ an emollient and/or a softening agent and/or a regenerating agent and/or a cicatrising agent and/or an astringent product and/or a softening agent and/or a moisturizing agent and/or a cleansing agent.

12 Claims, No Drawings

COMPOSITIONS FOR COUNTERACTING THE DEGRADATIONS AND INCONVENIENCE OF PERSPIRATION

This application is a continuation of application Ser. No. 821,879, filed on Jan. 27, 1986, now abandoned and a continuation of application Ser. No. 481,241, filed Apr. 1, 1983, now abandoned.

BACKGROUND OF THE INVENTION

The present invention relates to a novel composition enabling the degradations of body perspiration and more particularly of perspiration of the feet to be counteracted and the successful treatment for a long period of the drawbacks due to even excessive perspiration.

Perspiration is favoured by clothing, gloves, shoes and certain special equipment which reduce the possibility of its dissipation from an organism by preventing the heat losses necessary for the latter, which has the result of increased physiological effort, and consequently, more abundant perspiration, multiplied by effort, environment and condition.

The hyperhydrosis thus encourage causes maceration and all its drawbacks, certain of which are apparently anodyne such as unpleasant smells, softness of the skin which makes the epidermis tender and causes abrasions, blisters arising from friction and weight of the body, intertrigo by the pressure of the toes pressed against one another, soft corns, the formation of fungi, cutaneous mycosis, even of glandular hemmorrhage, all inconveniences which render walking sometimes very painful, also disturb neighbor equilibrium of the hydrolytic mantle of the skin. It also produces heating and intolerance of apparencies and very often thwarts protection against cold.

The sweat secreted by the inflamed sweat glands (developed normally after sexual maturity) contains nitrogenous substances, fats, water and salt. It may even contain elements of the epidermis. At the time of secretion, the sweat is in the form of a slightly opalescent, colorless liquid having an odor. It is normally acid in reacton by reason of the presence of fatty acids and of acid phosphates of sodium and of potassium. The body through its temperature and humidity encourages the development of certain microorganisms which, through their metabolism, decompose the organic substances found in the sweat. The fatty acids and their degradation products are responsible for the unpleasant odor of the sweat; these undesirable phenomena are provoked by bacteria which grow all the better as the perspiration becomes more abundant following excessive secretion of overactive and inflamed sweat glands.

The various antiperspirant all desordorising hiding products known until now only counter one, or maybe several of the causes, degradations and inconveniences mentioned above and can only act imperfectly, very little, or partially and almost always for short periods, and can even be without effect with respect to certain abrasions or to certain individuals. These products known in the prior art, which do which are not concerned with attacking the causes of the perspiration and do not take care even of the state in which the epidermis is after their use, are sometimes composed, even as regards so called body hygiene products, of toxic substances (listed in tables A, B and C established by the MINISTRY OF HEALTH) subject to regulated conditions of use in cosmetic products or body hygiene products.

GENERAL DESCRIPTION OF THE INVENTION

According to the present invention, there is provided a composition enabling the degradations and inconveniences of perspiration to be counteracted, said composition comprising at least one anti-absorbant agent and/or an antiseptic agent and/or an anti-sweating agent and/or an antiseptic and/or an anti-mycotic agent and/or an anti-irritant and/or an anti-jungal agent and/or an anti-putrid agent and/or a deodorizing agent and/or an nutrient agent and/or an emollient and/or a softening agent and/or a regenerating agent and/or a cicatrising agent and/or an astringent substance and and/or a softening agent and/or a moisturizing agent and/or a cleansing agent.

DESCRIPTION OF PREFERRED EMBODIMENTS

In accordance with the invention, the composition comprises at least one of the following agents:

(a) an absorbant agent adapted to dry the excess of moisture in proportions very much higher than the weight and which can itself lose this moisture by evaporation, and may be, for example, a kaolin, clay, bentonite, calcium carbonate, aluminum or zirconium hydrochloride, a polymer or "chlorhydrol" (aluminum salt).

(b) a supporting agent, also absorbant and softening, unfermentable such as magnesium silicate, talc, for example;

(c) a softening and fatty agent restoring elastisty to the tissues and/or fats and/or absorbant such as natural kaolin, for example;

(d) a nutrient and emollient agent, and/or absorbant such as rice starch, corn starch, wheat starch, for example;

(e) a cicatrizing agent eliminating callosities and acting on cellular regulation whilst moistening the skin such as allantoin, urea, aristol, for example;

(f) an anti-irritant agent, calming, deodorizing agent, such as alkphaketoglutaric acid, for example, and/or for skin protection such an oxide and/or an hydroxide, an oxide and/or peroxide of titanium, for example;

(g) a deodorizing, absorbant agent such as: slightly calcined magnesia, peroxide, perborate of magnesia, sodium chlorate, citric acid or acetylcitric acid, an aliphatic hydrocarboxylic acid, vitamin $B_3$, cyanocobalamin acid, nicotinic acid, B pyridine carbonic acid, for example;

(h) a cleansing, antiseptic, antiputrid, astringent and deodorizing agent such as tannic acid, alum, zinc oxide and peroxide, naphthol acetotartrate, aluminium disulfovinate, for example;

(i) an antibiotic, antifungal agent, such as "Fongeryl", "Nystatine", mycostatin, asterol, B-amphoteriane, fungizone;

(j) a antibacterial, antimycosic agent, such as: benzoic acid, formic aldehyde, salicylic acid, for example;

(k) a preservative agent for a dermatological preparation, such as: prodhyseptine, an orthohydroxybenzoic acid ester, for example;

(l) a vitamin agent such as vitamin $B_5$, $B_2$,$B_3$, or the vitamin P.P,L,E,F,P.

(m) a supplementary agent which increases the adherence to the skin such as magnesium stearate, for example;

(n) a suitable perfume;

(o) a suitable coloring agent.

In a preferred embodiment of the composition according to the invention, the antibacterial, antifungal and antimycosic agents are constituted by association of methyl, propyl and butyl parahydroxybenzoate, which constitute, in addition, conjointly a preservative agent for dermatological preparations.

In another preferred embodiment of the composition according to the invention, this one comprises the constituents enumerated above, present in the following proportions:

| | |
|---|---|
| antiseptic agent | from 5.00 to 25.00% |
| antibactericide (a) | from 0.00 to 7.50% |
| antiperspirant | from 2.00 to 20.00% |
| deodorant | from 2.00 to 20.00% |
| absorbant | from 10.00 to 40.00% |
| astringent | from 5.00 to 35.00% |
| cicatrising agent | from 0.00 to 8.00% |
| nutrient agent | from 2.00 to 15.00% |
| softening agent | from 0.00 to 8.00% |
| anti-irritant agent | from 0.00 to 8.00% |
| regenerating agent | from 0.00 to 8.00% |
| moisturizing and/ or oxygenizing agent | from 0.00 to 8.00% |
| adherent agent | from 0.00 to 10.00% |
| vitamin | from 0.00 to 10.00% |
| preservative | from 0.00 to 3.00% |

A preferred formula of the composition according to the invention has the following qualitative and quantitative formulation:

| | |
|---|---|
| methyl para-hydroxybenzoate | from 0.00 to 2.50% |
| propyl para-hydroxybenzoate | from 0.00 to 2.50% |
| butyl para-hydroxybenzoate | from 0.00 to 2.50% |
| zinc ricinoleate or undecylenate | from 0.00 to 8.00% |
| allantoin | from 0.00 to 8.00% |
| alpha-ketoglutaric acid | from 0.00 to 8.00% |
| tannic acid | from 5.00 to 35.00% |
| potassium alum | from 5.00 to 35.00% |
| kaolin | from 10.00 to 40.00% |
| rice starch | from 2.00 to 25.00% |
| light calcined magnesia | from 0.00 to 20.00% |
| magnesium stearate | from 0.00 to 30.00% |
| magnesium silicate | from 10.00 to 30.00% |
| folic acid | from 0.00 to 4.00% |
| cyanocobalamin | from 0.00 to 4.00% |
| linolenic acid | from 0.00 to 4.00% |

A particularly preferred formula of the composition according to the invention may have the following qualitative and quantitative formulation:

| | |
|---|---|
| methyl para-hydroxybenzoate | about 0.070% |
| propyl para-hydroxybenzoate | about 0.050% |
| butyl para-hydroxybenzoate | about 0.030% |
| benzoic acid | about 2.% |
| tannic acid | about 2% |
| potassium alum | about 10% |
| zinc oxide | about 5% |
| kaolin | about 34% |
| rice starch | about 5% |
| light calcined magnesia | about 8% |
| talc | about 20% |
| magnesium stearate | about 5% |
| allantoin | about 2% |
| alpha-ketoglutaric acid | about 0.850% |
| chlorhydrol | about 6% |

The composition according to the invention is prepared in the form of powder, ointment, cream, stick, liquid, aerosol, soap, etc . . . adapted for application to the skin to exercise its effect of countering the degradations and inconveniences of perspiration. The preparation of the composition according to the invention is effected by mixing the constituents, if necessary associated with suitable supports or vehicles.

The composition according to the invention enables a maceration to be treated at no matter what stage of its development and the achievement of excellent results, of which the effects continue for a very long duration.

The treatment is very simple and unrestrictive It suffices, in general, in the large majority of cases, to place in contact with the skin about 2.5 grams of this product every morning, and to leave it there for the day; then repeating the same operation six succesive mornings and this only twice a year to each foot. Exceptionally for particularly resistant cases, three times may be necessary in the first year.

The composition according to the present invention may be used in all cases as a disinfectant, bactericide, deodorant, cicatrising, anti-inflamation agent, absorbant, softener, regenerating agent, astringent, suppleness agent, moisturizer, cleanser, emollient, nutrient, anti-irritant, antiseptic agent, antiputrid agent, antifungal agent, anti-mycotic agent, anti-perspirant and hygienic agent, in particular against the degradations and drawbacks of perspiration, in powder, in liquid, in a solid block, stick, cream, ointment, rouge, lacquer, as a fumigenic vapor, soap, shampoo, cosmetic, processing of fabrics, textiles, papers, plastic materials and the like for bandages, plasters, coated or impregnated in any way and by any preparation. It can serve as a remedy, for maintenance care, for beauty treatment by contact, by message, by friction, and by applications of any kinds to the body and to the skin.

The composition according to the invention may have a great effectiveness over a very long period by reason, not only of the action itself of each of its constituents, but especially the synergy of action between its various constituents which determines a reciprocal increase in activity of said constituents and preserves or improves the condition of the dermis, of the epidermis, and of the sweat glands.

As emerges from the foregoing, the invention is no way limited to those of its types of application, embodiments and uses which have just been described more explicitely; it encompasses on the contrary all modifications which may come to the spirit of the technician skilled in the art, without departing from the framework nor the scope of the present invention.

We claim:

1. A foot anti-perspirant composition having a long-lasting effect, which comprises:
   (a) an effective amount of at least one agent which absorbs excess moisture and which is selected from the group consisting of clay, calcium carbonate, aluminum hydrochloride and zirconium hydrochloride;
   (b) an effective amount of at least one support agent, which is also an absorbent and softening agent which is not fermentable, and which is selected from the group consisting of magnesium silicate and talc;
   (c) an effective amount of at least one deodorizing and absorbent agent selected from the group consisting of calcined magnesia, peroxide, magnesium perborate, sodium chlorate, a citric acid, citric ester, acetyl citric acid, acetyl citric ester, an aliphatic hydroxy carboxylic acid ester, vitamin $B_3$, cyanocobalamin acid, nicotinic acid and β-pyridine carbonic acid;

(d) an effective amount of at least one nutrient and emollient agent selected from the group consisting of rice starch, corn starch and wheat starch;

(e) an effective amount of at least one antiseptic agent which also exhibits anti-putrid, astringent and deodorizing effects, which is selected from the group consisting of tannic acid, alum, zinc oxide, peroxide, acetotartrate, naphthol and aluminum disulfovinate; and (f) an effective amount of at least one antimycotic agent selected from the group consisting of diamthazole dihydrochloride and amphotericin B; or an effective amount of at least one anti-bacterial agent selected from the group consisting of benzoic acid, formaldehyde and salicylic acid; or a mixture of the above; or an effective amount of a mixture containing methyl, propyl and butyl parahydroxy-benzoate which functions, in addition, as a preserving agent.

2. The composition of claim 1, which further comprises a cicatrising agent acting as a cellular regulator and hydrating agent and which is selected from the group consisting of allantoin, urea and thymol iodide.

3. The composition of claim 1, which further comprises an anti-irritant and sedative agent selected from the group consisting of α-ketoglutaric acid, zinc oxide, zinc hydroxide, titanium oxide and peroxide.

4. The composition of claim 1, which further comprises an agent which increases adhesion to the skin.

5. The composition of claim 1, which further comprises a softening agent which restores elasticity to the skin.

6. The composition of claim 4, wherein said adhesion-increasing compound is magnesium stearate.

7. The composition of claim 1, which further comprises a preserving agent selected from the group consisting of prodhyseptine and esters of orthohydroxybenzoic acid.

8. The composition of claim 1, which further comprises a vitamin selected from the group consisting of vitamins $B_5$, $B_2$, $B_3$, PP, L, E, F and P.

9. The composition of claim 1, which comprises in wt.%:
antiseptic agent, from 5.00 to 25%
antibactericidal agent, from 0.00 to 7.50%
antiperspirant agent, from 2.00 to 20.00%
deodorant agent, from 2.00 to 20.00%
absorbent agent, from 10.00 to 40.00%
astringent agent, from 5.00 to 35.00%
cicatrising agent, from 0.00 to 8.00%
nutrient agent, from 2.00 to 15.00%
softening agent, from 0.00 to 8.00%
anti-irritant agent, from 0.00 to 8.00%
regenerating agent, from 0.00 to 8.00%
moisturizing and/or
    oxygenizing agent, from 0.00 to 8.0%
adherent agent, from 0.00 to 10.00%
vitamin agent, from 0.00 to 10.00%; and
preservative agent, from 0.00 to 3.00%.

10. The composition of claim 1, which comprises in wt.%:
methyl para-hydroxybenzoate, from 0.00 to 2.50%,
propyl para-hydroxybenzoate, from 0.00 to 2.50%,
butyl para-hydroxybenzoate, from 0.00 to 2.50%,
zinc ricinoleate or undecylenate, from 0.00 to 8.00%,
allantoin, from 0.00 to 8.00%,
α-ketoglutaric acid, from 0.00 to 8.00%,
tannic acid, from 5.00 to 35.00%,
potassium alum, from 5.00 to 35.00%,
kaolin, from 10.00 to 40.00%,
rice starch, from 2.00 to 15.00%,
light calcined magnesia, from 2.00 to 20.00%,
magnesium stearate, from 0.00 to 10.00%,
magnesium silicate, from 10.00 to 30.00%,
folic acid, from 0.00 to 4.00%,
cyanocobalamin, from 0.00 to 4.00%, and
linolenic acid, from 0.00 to 4.00%.

11. The composition of claim 1, which comprises in wt.%:
methyl para-hydroxybenzoate, about 0.070%,
propyl para-hydroxybenzoate, about 0.050%,
butyl para-hydroxybenzoate, about 0.030%,
benzoic acid, about 2%,
tannic acid, about 2%,
potassium alum, about 10%,
zinc oxide, about 5%,
kaolin, about 34%,
rice starch, about 5%,
light calcined magnesia, about 8%,
talc, about 20%,
magnesium stearate, about 5%,
allantoin, about 2%,
α-ketoglutaric acid, about 0.850%, and chlorhydrol, about 6%.

12. The composition of claim 1, wherein said clay absorbing excess moisture is selected from the group consisting of kaolin and bentonite.

* * * * *